United States Patent [19]

Wyatt et al.

[11] 4,341,870
[45] Jul. 27, 1982

[54] CULTIVATABLE HUMAN ROTAVIRUS TYPE 2

[75] Inventors: Richard G. Wyatt, Potomac; Walter D. James, Beltsville, both of Md.; Edward H. Bohl, Wooster, Ohio; Kenneth W. Theil, Wooster, Ohio; Linda J. Saif, Wooster, Ohio; Anthony R. Kalica, Rockville, Md.; Harry B. Greenberg, Washington, D.C.; Albert Z. Kapikian, Rockville, Md.; Robert M. Chanock, Bethesda, Md.

[73] Assignee: The United States of America as represented by the Secretary of the Department of Health & Human Services, Washington, D.C.

[21] Appl. No.: 208,389

[22] Filed: Nov. 19, 1980

[51] Int. Cl.³ .................... C12N 7/08; A61K 39/12
[52] U.S. Cl. .................................... 435/237; 424/89
[58] Field of Search .......................... 424/89; 435/237

[56] References Cited

PUBLICATIONS

McNulty-J. Gen. Virol., vol. 40, No. 1, (1978) pp. 1 & 6-8.
Wyatt et al., Perspectives in Virology, vol. 10, Raven Press, New York, 1978, pp. 121-145.
Kapikian et al., The Am. Journal of Clinical Nutrition, vol. 31, Dec. 1978, pp. 2219-2236.
Babiuk et al., Journal of Clinical Microbiology, 6(6):610-617, Dec. 1977.
Theil et al., American Journal Veterinary Research, 38:1765-1768, 1977.
Almeida et al., Journal of General Virology, 40:213-218, 1978.
Kapikian, et al., Diagnostic Procedures for Viral, Rickettsial and Chlamydial Infections, 5th ed., Lennette et al. (eds.), Am. Public Health Assoc., Wash., DC, pp. 941-942, 1979.
Barnett et al., Journal of Clinical Microbiology, 10:111-113, 1979.
McNulty et al., Archives of Virology, 61:13-21, 1979.
Drozdov et al., Vopr. Virusol., 4:389-92, 1979.
Theil et al., American Journal of Veterinary Research, 41:140-143, 1980.
Wyatt et al., Science, 207:189-191, Jan. 11, 1980.
Kapikian et al., Reviews of Infectious Diseases, 2(3):459-469, 1980.

Primary Examiner—Sam Rosen
Attorney, Agent, or Firm—John S. Roberts, Jr.

[57] ABSTRACT

This invention relates to a precursor or intermediate for a rotavirus vaccine to protect infants and young children against diarrhea caused by rotavirus. The invention is the efficient propagation of a strain of human rotavirus type 2 prepared by a method of cultivation by multiple passages in vivo in gnotobiotic piglets and by multiple passages in vitro subsequently in AGMK (African green monkey kidney) cell cultures. Additionally, rotavirus is treated with a biologically active amount of trypsin prior to growth in AGMK cells, and the inoculated cell cultures are centrifuged at a low centrifugal force before incubation.

2 Claims, 1 Drawing Figure

PROPAGATION OF HUMAN ROTAVIRUS TYPE 2 ("WA" STRAIN)

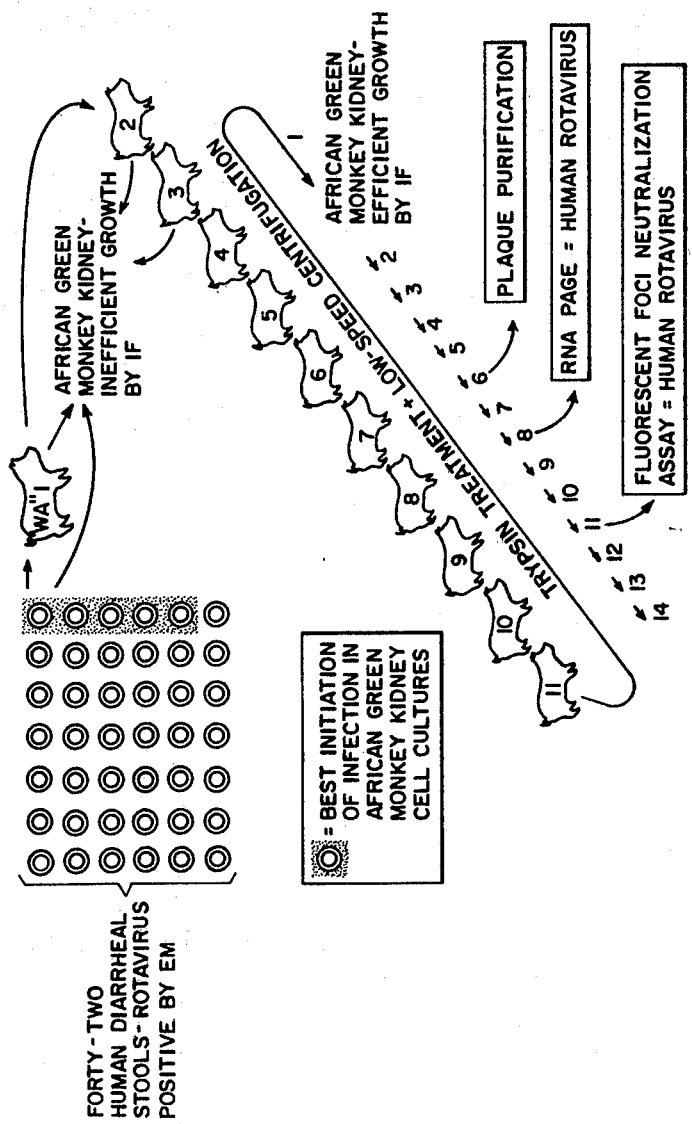

CULTIVATABLE HUMAN ROTAVIRUS TYPE 2

The present invention relates to an improvement in a strain of type 2 human rotavirus (Wa strain), which led to efficient growth of the virus in AGMK cells to a relatively high titer during mutiple passage. The passage series was initiated with virus that first had been passaged 11 times serially in newborn gnotobiotic piglets. Prior to each passage in cell culture, the virus was treated with trypsin and the inoculated cultures were centrifuged at a low speed. The efficient cultivation of this type 2 rotavirus provides a strain of human rotavirus for use in development of immunoprophylaxis for a serious diarrheal disease of human infants and young children.

Starting material is available as "Wa" rotavirus type 2 in the freezers of the Laboratory of Infectious Diseases, NIH, at Building 7 on the NIH reservation, Bethesda, Md.

PRIOR ART STATEMENT

Wyatt, et al., *Perspective in Virology*, Vol. 10, Raven Press, New York, 1978, passages 121-145.

Kapikian et al., "Viral Diarrhea. Etiology and Control," *The American Journal of Clinical Nutrition*, Vol. 31, December 1978, pages 2219-2236.

Babiuk et al., "Rotavirus Isolation and Cultivation in the Presence of Trypsin," *Journal of Clinical Microbiology*, 6(6):610-617, December 1977.

Theil, K. W., E. H. Bohl and A. G. Agnes, "Cell Culture Propagation of Porcine Rotavirus (Reovirus-like Agent)," *American Journal Veterinary Research*, 38:1765-1768, 1977.

Almeida, J. D., T. Hall, J. E. Bantvala, B. M. Totterdell, and I. L. Chrystie, "The Effect of Trypsin on the Growth of Rotavirus," *Journal of General Virology*, 40:213-218, 1978.

Kapikian, A. Z., R. H. Yolken, H. B. Greenberg, R. G. Wyatt, A. R. Kalica, R. M. Chanock, and H. W. Kim, "Gastroenteritis Viruses," in *Diagnostic Procedures for Viral, Rickettsial and Chlamydial Infections*, 5th edition, E. H. Lennette and N. J. Schmidt (eds.), American Public Health Association, Washington, D.C., pp. 941-942, 1979.

Barnett, B. B., R. S. Spendlove and M. L. Clark, "Effect of Enzymes on Rotavirus Infectivity," *Journal of Clinical Microbiology*, 10:111-113, 1979.

McNulty, M. S., G. M. Allan, D. Todd, and J. B. McFerran, "Isolation and Cell Culture Propagation of Rotaviruses from Turkeys and Chickens," *Archives of Virology*, 61:13-21, 1979.

Drozdov, S. G., L. A. Shekoian, M. V. Korolev, and A. G. Andzhaparidze, "Human Rotavirus in Cell Culture: Isolation and Passage," *Vopr. Virusol.*, 4:389-92, 1979.

Theil, K. W. and E. H. Bohl, "Porcine Rotaviral Infection of Cell Culture: Effects of Certain Enzymes," *American Journal of Veterinary Research*, 41:140-143, 1980.

Wyatt et al., "Human Rotavirus Type 2: Cultivation in Vitro," *Science*, 207:189-191, Jan. 11, 1980.

Kapikian et al., "Approaches to Immunization of Infants and Young Children Against Gastroenteritis Due to Rotaviruses," *Reviews of Infectious Diseases*, 2(3):459-469, 1980.

The Babiuk, Theil, Almeida, Barnett, McNulty and Drozdov articles are noted for disclosure purposes, since a portion of the present invention involves treatment with trypsin. The report of successful cultivation of human rotavirus by Almeida et al. and Drozdov et al. was not confirmed on subsequent evaluation of viral RNA.

DESCRIPTION OF THE DRAWING

The FIGURE is a schematic diagram of the experimental strategy that led to the cultivation of the "Wa" strain of human rotavirus type 2 (EM=electron microscopy; IF=immunofluorescence; PAGE=polyacrylamide gel electrophoresis).

EXAMPLE 1

Generalized Process

Forty-two human rotavirus-positive stool samples were tested for their efficiency in initiating infection in African green monkey kidney cells; five of the stool specimens induced the production of antigens in $\geq 10\%$ of the cells. One of these strains, designated "Wa," was passaged 11 times in gnotobiotic piglets. After treatment with trypsin, virus from the 11th passage was inoculated into African green monkey kidney cells, which were then subjected to low-speed centrifugation. The virus grew efficiently in culture and has been serially passaged 14 to 25 times in African green monkey kidney cells. Emphasis has been placed on passage 16 to test for attenuation. Attempts to serially propagate the virus present in the original stool filtrate as well as in the intestinal contents of the first-, second-, or third-passage piglets were unsuccessful even though trypsin treatment and low-speed centrifugation were employed; such enzyme treatment and/or low-speed centrifugation were employed to facilitate propagation of rotavirus. Thus, it appeared that a mutant capable of efficient growth in cell culture had been selected during the 11 serial passages in piglets. The tissue culture-adapted strain was shown to be of human origin by polyacrylamide gel analysis of its RNA and by cross-neutralization studies. The next step forward from the development of this invention is to determine whether this type 2 rotavirus is attenuated for humans.

In developed countries, rotaviruses are the most important group of pathogens causing severe diarrhea in infants and young children. Thus, it is clear that a vaccine is indicated for such countries. In developing countries, rotaviruses are also of major importance as etiologic agents of gastroenteritis of infants and young children. Thus, an attenuated vaccine will probably prove useful in developing countries as well. The need for a live attenuated vaccine which would be administered by the oral route is indicated by the likely prime role of local intestinal immunity in resistance to rotavirus disease.

EXAMPLE 2

Studies were performed to establish the identity of the Wa tissue culture-adapted virus. Previous experience by some of us and others as well indicated the ease with which cultures could become contaminated with animal rotaviruses well-adapted to tissue culture that were also under study in the laboratory. The identity of the culture-adapted Wa strain was investigated by co-electrophoresing its viral RNA with that of other rotaviruses whose RNA gel patterns had been characterized previously. The RNA from the Wa isolate after eight passages in AGMK cultures was compared with RNA from the following rotraviruses: human rotavirus strains D and L; bovine rotavirus strains UK and NCDV; porcine rotavirus strains OSU and EE; simian rotavirus SA-11; and O agent. The RNA gel pattern of the Wa strain differed from each of the animal rotavirus RNA patterns in the mobility of three to seven genome segments. The Wa strain RNA differed from the D strain of type 2 human rotavirus in the mobility of only one segment, and its pattern was identical to that of the L strain of type 2 human rotavirus. The last pattern represents one of three previously recognized human rotavirus RNA gel patterns.

The Wa strain at the 11th culture passage was also compared to bovine, porcine, and simian rotaviruses by neutralization in tissue culture. Antibody assays for the animal rotaviruses were performed by plaque reduction. Bovine and simian rotaviruses were treated with trypsin (10 μg/ml, final concentration) prior to being incubated with diluted serum (1 hour at 37° C.) and inoculated onto CV-1 cells (a line derived from AGMK). The porcine rotavirus plaque reduction test was performed in MA 104 cells (a line derived from embryonic rhesus monkey kidney) by a procedure in which the agar overlay contained pancreatin (0.15 percent of 2.5 percent pancreatin 4×N.F.; Gibco) and DEAE dextran (100 μg/ml). The Wa strain did not produce plaques reproducibly in AGMK cells and for this reason neutralization was assayed by the technique of reduction of immunofluorescent foci similar to that described by Thoules et al., Arch. Virol., 53:287 (1977).

The bovine, simian, and procine rotaviruses were distinct from the Wa cell culture-adapted strain when tested by virus neutralization (Table 1 below). However, there was a one-way antigenic relationship between the simian virus and the Wa isolate; this is consistent with an observation made by immune electron microscopy. There was also a one-way antigenic relationship between the porcine and simian rotaviruses. The Wa culture-adapted virus was typed by ELISA and identified as serotype 2, the same type as the rotavirus present in the stool of the original patient. Thus, the tissue-grown Wa strain appears to be type 2 human rotavirus and not a tissue culture-adapted animal rotavirus contaminant acquired in the laboratory.

Cultivation of type 2 human rotavirus in tissue culture will facilitate a more detailed examination of its properties and permit manipulation of its genome with the intent of developing attenuated mutants for use in the prevention of a serious diarrheal disease of human infants.

TABLE 1

Serologic relation between tissue culture denoted Wa strain of rotavirus and rotaviruses of simian, bovine, and porcine origin. Homologous values are underlined; values for serum samples containing antibody against SA-11 and OSU rotaviruses present geometric mean values of two determinations. An additional test (without centrifugation) with the Wa strain and the UK, SA-11, OSU, and paired Wa serum samples confirmed the relationships shown here.

| Immunizing Rotavirus | Serum | | Reciprocal of antibody titer with indicated virus | | | |
|---|---|---|---|---|---|---|
| | Animal | Type | UK* | SA-11* | OSU* | Wa+ |
| Bovine, UK strain | Guinea pig | Hyperimmune | 7,606 | <160 | <160 | <160 |
| Bovine, NCDV strain | Guinea pig | Hyperimmune | ≧40,960 | 694 | 778 | <160 |
| Simian, SA-11 strain | Guinea pig | Hyperimmune | <20 | ≧40,960 | <160 | 640 |
| Porcine, OSU strain | Gnotobiotic piglet | Convalescent | <20 | 937 | 1,691 | 20 |
| Human type 2 Wa strain | Gnotobiotic piglet | Preinfection | <20 | 23 | <20 | 80 |
| Human type 2 Wa strain | Gnotobiotic piglet | Convalescent | 51 | 343 | <20 | 1,280 |

*Sixty percent plaque reduction.
+Sixty percent reduction of fluorescent foci. These titers were confirmed by plaque reduction when the plaque technique was subsequently developed for the Wa strain.

We claim:

1. A precursor for a diarrhea vaccine which is a human rotavirus type 2 prepared by a method of cultivation of the Wa strain of human rotavirus type 2 through eleven passages in vivo using gnotobiotic piglets, then taking that virus and passing it through 14 to 25 passages in vitro in African green monkey kidney cell cultures; and wherein prior to each of said kidney cell cultures the rotavirus is treated with an effective amount of trypsin and where at each passage the tissue culture inoculated with rotavirus is subjected to low force centrifugation.

2. The method according to claim 1 wherein the number of passages through African green monkey kidney is 16.

* * * * *